US00PP21343P2

(12) United States Plant Patent
Barends

(10) Patent No.: US PP21,343 P2
(45) Date of Patent: Sep. 28, 2010

(54) ***OSTEOSPERMUM* PLANT NAMED 'FIDOSTLIL'**

(50) Latin Name: *Osteospermum ecklonis*
Varietal Denomination: Fidostlil

(75) Inventor: Eveline Barends, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 12/455,105

(22) Filed: May 27, 2009

(51) Int. Cl.
*A01H 5/00* (2006.01)

(52) U.S. Cl. ..... Plt./360

(58) Field of Classification Search ..... Plt./360
See application file for complete search history.

*Primary Examiner*—Susan B McCormick Ewoldt
(74) *Attorney, Agent, or Firm*—C. A. Whealy

(57) ABSTRACT

A new and distinct cultivar of *Osteospermum* plant named 'Fidostlil', characterized by its compact and mounding plant habit; relatively short internodes; freely branching growth habit; freely and early flowering habit; large daisy-type inflorescences with lavender pink-colored ray florets; and good garden performance.

1 Drawing Sheet

Botanical designation: *Osteospermum ecklonis.*
Cultivar denomination: 'Fidostlil'.

BACKGROUND OF THE INVENTION

The present invention relates to a new and distinct cultivar of *Osteospermum* plant, botanically known as *Osteospermum ecklonis*, and hereinafter referred to by the name 'Fidostlil'.

The new *Osteospermum* plant is a product of a planned breeding program conducted by the Inventor in De Lier, The Netherlands. The objective of the program is to create and develop new *Osteospermum* cultivars with compact growth habit, freely branching and freely flowering habit and attractive inflorescence coloration.

The new *Osteospermum* plant originated from a cross-pollination by the Inventor in May, 2005 of two unnamed proprietary selections of *Osteospermum ecklonis*, not patented. The new *Osteospermum* was discovered and selected by the Inventor as a single flowering plant within the progeny of the stated cross-pollination in a controlled greenhouse environment in De Lier, The Netherlands in October, 2005.

Asexual reproduction of the new *Osteospermum* plant by terminal cuttings in a controlled greenhouse environment in De Lier, The Netherlands since November, 2005, has shown that the unique features of this new *Osteospermum* plant are stable and reproduced true to type in successive generations.

SUMMARY OF THE INVENTION

Plants of the new *Osteospermum* have not been observed under all possible environmental conditions. The phenotype may vary somewhat with variations in environment such as temperature and light intensity, without, however, any variance in genotype.

The following traits have been repeatedly observed and are determined to be the unique characteristics of 'Fidostlil'. These characteristics in combination distinguish 'Fidostlil' as a new and distinct cultivar of *Osteospermum*:

1. Compact and mounding plant habit.
2. Relatively short internodes.
3. Freely branching growth habit.
4. Freely and early flowering habit.

5. Large daisy-type inflorescences with lavender pink-colored ray florets.
6. Good garden performance.

Plants of the new *Osteospermum* differ from plants of the parent selections primarily in plant and growth habit as plants of the new *Osteospermum* are more compact in plant habit and more uniform in growth habit than plants of the parent selections.

Plants of the new *Osteospermum* can be compared to plants of the *Osteospermum* 'Margarita Rosita', not patented. In side-by-side comparisons conducted in De Lier, The Netherlands, plants of the new *Osteospermum* differed from plants of 'Margarita Rosita' in the following characteristics:

1. Plants of the new *Osteospermum* were more freely branching than plants of 'Margarita Rosita'.
2. Plants of the new *Osteospermum* flowered earlier than plants of 'Margarita Rosita'.
3. Plants of the new *Osteospermum* were not as rounded as apices of ray florets of plants of 'Margarita Rosita'.
4. Plants of the new *Osteospermum* had less tendency to stretch than plants of 'Margarita Rosita'.

BRIEF DESCRIPTION OF THE PHOTOGRAPH

The accompanying photograph illustrates the overall appearance of the new *Osteospermum*. This photograph shows the colors as true as it is reasonably possible to obtain in colored reproductions of this type. Colors in the photograph may differ slightly from the color values cited in the detailed botanical description which accurately describe the colors of the new *Osteospermum*. The photograph comprises a side perspective view of a typical flowering plant of 'Fidostlil' grown in a container.

DETAILED BOTANICAL DESCRIPTION

The aforementioned photograph, following observations and measurements describe plants grown in De Lier, The Netherlands during the spring and early summer in a glass-covered greenhouse and under conditions and practices which approximate those generally used in commercial *Osteospermum* production. During the production of the plants, day temperatures ranged from 17° C. to 35° C. and night temperatures ranged from 15° C. to 25° C. Plants were pinched one time. Plants were nine weeks old when the photograph and description were taken. In the following description, color references are made to The Royal Horticultural Society Colour Chart, 2001 Edition, except where general terms of ordinary dictionary significance are used.

Botanical classification: *Osteospermum ecklonis* 'Fidostlil'.

Parentage:

*Female, or seed, parent.*—Unnamed proprietary selection of *Osteospermum ecklonis*, not patented.

*Male, or pollen, parent.*—Unnamed proprietary selection of *Osteospermum ecklonis*, not patented.

Propagation:

*Type.*—Terminal vegetative cuttings.

*Time to initiate roots, summer.*—About six days at 22° C.

*Time to initiate roots, winter.*—About one week at 22° C.

*Time to produce a rooted cutting, summer.*—About twelve days at 22° C. to 30° C.

*Time to produce a rooted cutting, winter.*—About two weeks at 20° C. to 25° C.

*Root description.*—Medium in thickness, fibrous; whitish grey in color.

*Rooting habit.*—Moderate branching; moderately dense.

Plant description:

*Plant form/growth habit.*—Compact and mounding plant habit; relatively short internodes, dense and bushy growth habit; moderately vigorous growth habit.

*Plant height.*—About 16 cm to 18 cm.

*Plant diameter.*—About 24 cm.

*Lateral branches.*—Quantity per plant: Freely branching habit, when pinched, about nine primary lateral branches develop per plant. Length: About 12 cm to 14 cm. Diameter: About 4 mm. Internode length: Relatively short, about 2 mm to 6 mm. Strength: Strong, sturdy. Texture: Sparsely pubescent. Color: Close to 144A.

*Foliage description.*—Arrangement: Alternate, simple. Length: About 6 cm to 7 cm. Width: About 3 cm to 3.5 cm. Shape: Elliptic. Apex: Acute. Base: Attenuate. Margin: Lobed; serrate. Texture, upper surface: Smooth, glabrous. Texture, lower surface: Sparsely pubescent. Venation pattern: Pinnate. Color: Developing leaves, upper surface: Close to 137B. Developing leaves, lower surface: Close to 147B. Fully expanded leaves, upper surface: Close to 147A; venation, close to 144B. Fully expanded leaves, lower surface: Close to 147B; venation, close to 144B. Petiole: Length: About 1.5 cm. Diameter: About 3 mm to 4 mm. Texture, upper and lower surfaces: Smooth, glabrous. Color, upper surface: Close to 144B. Color, lower surface: Close to 144A.

Inflorescence description:

*Appearance.*—Daisy-type inflorescence form with elliptic to slightly obovate-shaped ray florets; inflorescences positioned beyond the foliage on moderately strong peduncles; inflorescences terminal and axillary; inflorescences face upright; ray and disc florets developing acropetally on a capitulum.

*Flowering habit.*—Freely flowering habit; about 10 to 40 inflorescences developing per plant.

*Fragrance.*—None detected.

*Flowering response.*—In The Netherlands, plants of the new *Osteospermum* flower continuously from spring to frost in the autumn; early flowering habit, plants begin flowering about eight weeks after planting.

*Inflorescence longevity.*—At temperatures of 14° C. to 20° C., inflorescences last about 2.5 weeks on the plant; inflorescences persistent.

*Inflorescence bud.*—Height: About 1.8 cm. Diameter: About 1.2 cm. Shape: Globular to ovoid. Color: Close to 137A.

*Inflorescence size.*—Diameter: About 7 cm to 7.5 cm. Depth (height): About 5 mm. Disc diameter: About 8 mm to 10 mm. Receptacle diameter: About 4 mm. Receptacle height: About 4 mm. Receptacle color: Close to 146A.

*Ray florets.*—Length: About 3.5 cm to 4 cm. Width: About 9 mm to 10 mm. Shape: Elliptic to slightly obovate. Apex: Rounded to slightly obtuse. Base: Attenuate. Margin: Entire. Texture: Smooth, glabrous; satiny. Number of ray florets per inflorescence/arrangement: About 18 to 20 in one to 1.5 whorls. Color: When opening, upper surface: Close to 76B. When opening, lower surface: Close to N88C; longitudinal stripes, close to N155D and 144A. Fully opened, upper surface: Close to 75A; color becoming closer to 77C with development. Fully opened, lower surface: Close to N87B; longitudinal stripes, close to N155D and 144A.

*Disc florets.*—Shape: Tubular; apex dentate, five-pointed. Length: About 5 mm to 7 mm. Diameter: About 2 mm. Number of disc florets per inflorescence: About 60 to 70. Color: Immature and mature: Apex: Close to 95C. Mid-section: Close to N77C. Base: Close to N155D.

*Phyllaries.*—Quantity per inflorescence: About 10 to 13 in a single whorl. Length: About 1 cm. Width: About 1 mm to 2 mm. Shape: Lanceolate. Apex: Acuminate. Base: Truncate. Margin: Entire. Texture, upper and lower surfaces: Sparsely pubescent. Color, upper surface: Close to 146A. Color, lower surface: Close to 138A.

*Peduncles.*—Length: About 8 cm to 9 cm. Diameter: About 2 mm. Strength: Moderately strong. Aspect: Upright. Texture: Pubescent. Color: Close to 144A.

*Reproductive organs.*—Androecium: Present on disc florets only. Anther shape: Lanceolate. Anther length: About 2 mm. Anther color: Close to N77A. Pollen amount: Moderate to abundant. Pollen color: Close to 23A. Gynoecium: Present on both ray and disc florets. Pistil length: About 1.5 cm. Stigma shape: Bi-parted. Stigma color: Close to 79A. Style length: About 8 mm. Style color: Close to 79A.

*Seeds/fruits.*—Seed and fruit development have not been observed on plants of the new *Osteospermum*.

Disease/pest resistance: Plants of the new *Osteospermum* have not been shown to be resistant to pathogens and pests common to *Osteospermums*.

Garden performance: Plants of the new *Osteospermum* have been observed to have good garden performance and to tolerate rain, wind and temperatures ranging from about 4° C. to about 35° C.

It is claimed:

1. A new and distinct *Osteospermum* plant named 'Fidostlil' as illustrated and described.

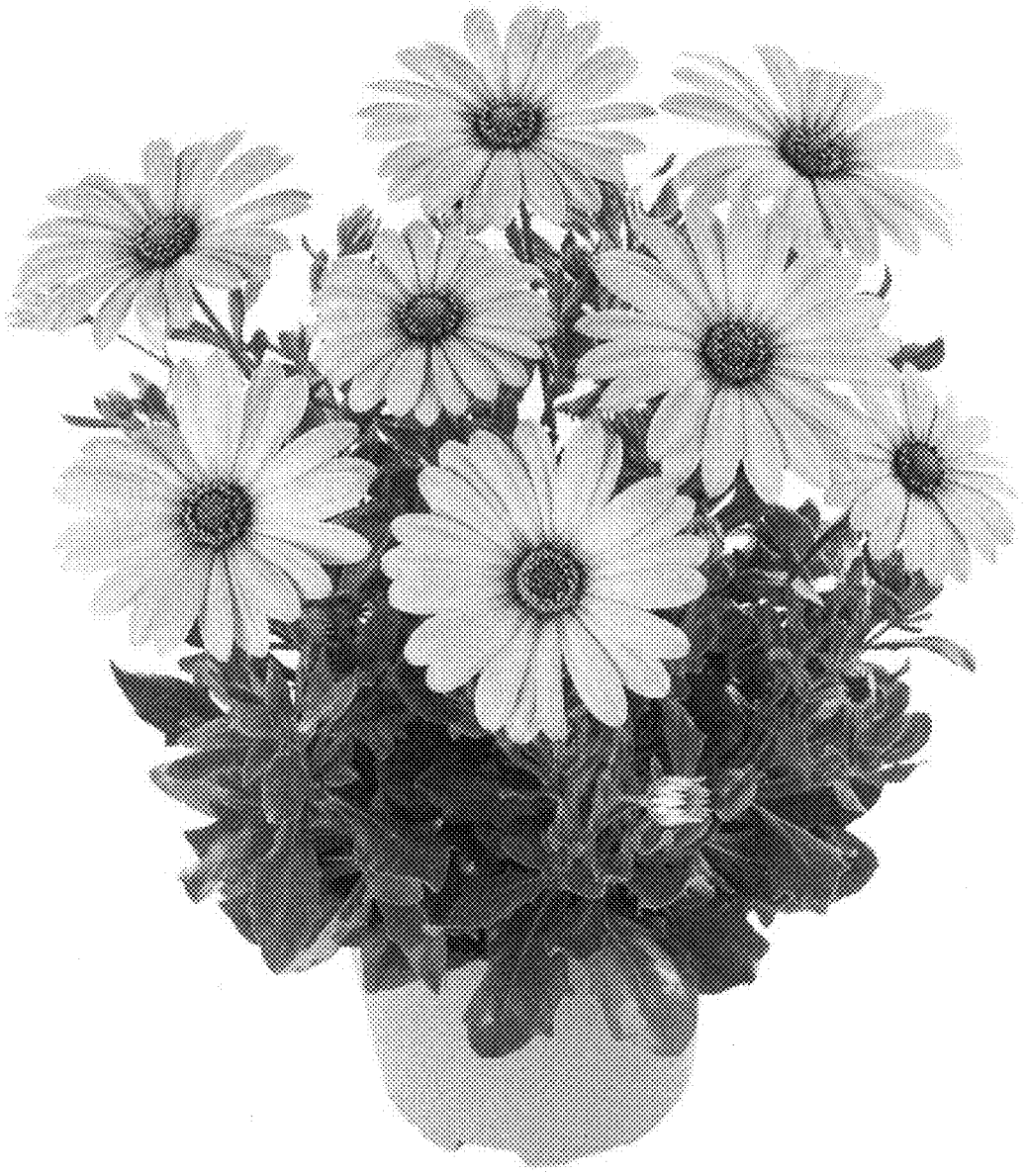

* * * * *